United States Patent [19]

Marciel

[11] Patent Number: Plant 7,581

[45] Date of Patent: Jul. 9, 1991

[54] MINIATURE POT ROSE NAMED DEMESI

[75] Inventor: Stanley G. Marciel, Aptos, Calif.

[73] Assignee: DeVor Nurseries, Inc., Watsonville, Calif.

[21] Appl. No.: 495,901

[22] Filed: Mar. 19, 1990

[51] Int. Cl.[5] ..... A01H 5/00

[52] U.S. Cl. ..... Plt./10

[58] Field of Search ..... Plt./10

*Primary Examiner*—James R. Feyrer

*Attorney, Agent, or Firm*—Charles W. Rummler

[57] ABSTRACT

A new and distinct miniature pot rose plant adapted for pot plant culture and particularly distinguished by its continuous and profuse production of medium size flowers of a Cardinal Red color from early Spring to Winter on a compact bush having a height of about 22 cm. when grown to the age of about 12 weeks in a 4 in. pot; this plant having abundant foliage.

1 Drawing Sheet

BACKGROUND OF THE NEW PLANT

This new miniature rose variety originated as a seedling of a hybrid produced by me at Pleasanton, Calif. by combining a plant selected from my collection of rose plants maintained for breeding purposes with a plant selected from the same collection as the pollen parent with the object of producing well balanced, profusely blooming plants for growth in a 4 in. pot. The present seedling was selected for propagation from those produced by seeds of the said hybrid because of its Cardinal Red flowers of very good size, shape and quantity for pot plant culture and because these flowers were produced from a compact bush of favorable height having abundant foliage and an apparently vigorous growth habit. Propagation of this selected seedling was done by me at Watsonville, Calif. by means of cuttings from the Pleasanton plant with such favorable results that this plant was reproduced through several successive generations which proved conclusively that the novel characteristics of the original selected seedling were retained from generation to generation and appeared to be firmly fixed.

DESCRIPTION OF THE DRAWING

This new miniature pot plant is illustrated by the accompanying photographic drawing which, in full color, shows a potted plant in full bloom with numerous flowers in various stages of development with color rendition as nearly true to that herein specified as is reasonably possible to obtain by conventional photographic procedures.

DESCRIPTION OF THE NEW VARIETY

The following is a detailed description of my new miniature pot rose based upon observation of greenhouse plants at Watsonville, Calif. with the color designations being according to The R.H.S. Colour Chart published by The Royal Horticultural Society of London, England.

THE PLANT

Origin: Seedling.

Parentage: Both the seed parent and the pollen parent were unnamed and unpatented plants selected from my collection of rose plants maintained at Pleasanton, Calif. for breeding purposes.

Classification:

*Botanic.*—Hybrid Miniature Rose.

*Commercial.*—Miniature Pot Rose.

Form: An upright free branching compact bush as grown in a 4 in. pot.

Height: About 22 cm. at the age of 12 weeks.

Growth: Upright, vigorous and free branching.

Main stem:

*Length.*—About 145 mm. from the last flower cut.

*Color.*—Yellow Green 144-A.

*Strength.*—Very sturdy for mini-flora bush.

Foliage:

*Character.*—Medium size.

*Quantity.*—Abundant.

*Number of leaves.*—8, from the last flower cut.

*Size.*—About 59 mm. long, in average, with 3 to 7 leaflets.

*Rachis.*—About 18 mm. for 3 part leaf and about 40 mm. for a 7 part leaf.

*Leaflets.*—Size: Average, about 26 mm. long and 15 mm. wide. Shape: Elliptic with denticulate margin. Texture: Leathery and smooth. Aspect: Almost glossy. Color: Upper side — Yellow Green 147-A. Under side — Yellow Green 147-B.

Ribs and veins: Depressed on upper side and slightly rounded on the lower side.

Thorns:

*Size.*—About 4 mm.

*Color.*—Greyed Red 182-B.

THE BUD

Size: Medium.

Shape: Oval.

Rate of opening: Slow.

Color of petals:

*When sepals first divide.*—Cardinal Red 53-A.

*When petals begin to unfurl.*—Red 53-C.

Sepals:

*Number.*—Five.

*Shape.*—Spreading with leafs protruding on each side.

*Character.*—The sepals spread outwardly when the flowers open and curl back as the bloom matures.

*Color.*—Inside — Yellow Green 147-C. Outside — Yellow Green 146-B.

Calyx:

*Shape.*—Funnel-shaped.

*Size.*—Medium.

*Splitting.*—Calyx does not split.
*Aspect.*—Smooth.
Peduncle of flower stem:
*Length.*—About 37 mm.
*Character.*—Erect and slender.
*Color.*—Yellow Green 144-B.

THE FLOWER

Blooming habit: Continuous and profusely from early Spring to Winter, blooming freely under greenhouse conditions.
Size of bloom: Small.
*Diameter.*—About 60 mm. wide.
*Depth.*—About 21 mm.
Borne: Singly.
Shape:
*When bloom first opens.*—High centered.
*When bloom matures.*—Nicely imbricated and slightly flattened.
Petalage:
*Number.*—29.
*Number of florets.*—8.
*Arrangement.*—Imbricated,
*Form.*—Cupped with entire margin and cuspidate apex.
*Texture.*—Leathery.
*Appearance.*—Velvety.
*Color.*—Outermost petals: Body — Current Red 46-A with base of 54-B. Inside petals: Body — Cardinal Red 53-A with base of 54-C. Reverse side — Cardinal Red 53-C.
*Petaloids.*—Number 10. Size: About 9 mm. Color: Cardinal Red 53-A with base of 54-C.
Peduncle of flower stem:
*Length.*—About 37 mm.

i Color.—Yellow Green 144-B.
*Character.*—Sturdy and upright.
Discoloration after full bloom: Slightly.
Persistence: The flowers hang on and dry.
Fragrance: Medium.
Disease resistance: Moderately resistant to mildew, rust and black spots as observed at Watsonville, Calif.
Lasting quality: Long lasting both on the plant and as a cut flower.

THE REPRODUCTIVE ORGANS

Stamens:
*Number.*—47.
*Arrangement.*—Slightly introrse.
*Anthers.*—Size: About 2 mm. Color: Yellow Orange 23-B.
*Filaments.*—Length: About 4 mm. Color: Yellow 5-D.
*Pollen.*—Color: Yellow Orange 23-B.
Pistils:
*Number.*—45.
*Styles.*—Length: About 7 mm. Color: Yellow 11-D tipped with Greyed Purple 186-A.
*Stigmas.*—Color: Yellow 18-D.
Character of the ovaries: Oval shaped and slightly flattented.

I claim:

1. The new and distinct miniature pot rose variety, substantially as herein shown and described, characterized by its continuous and profuse production of medium sized Cardinal Red flowers borne on strong upright stems of medium length growing from a small, compact, free branching bush having a height of about 22 cm. at an age of about 12 weeks.

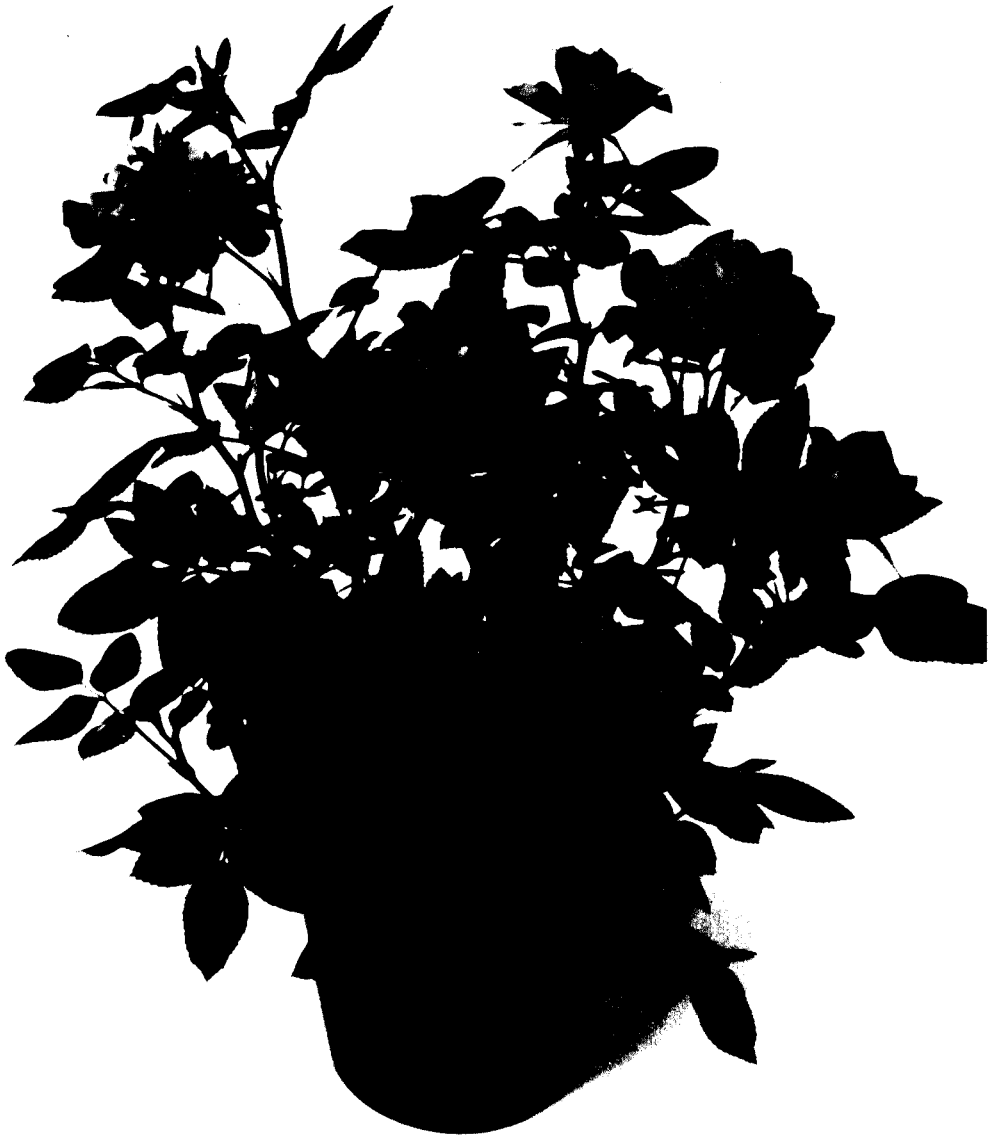

* * * * *